United States Patent
Chadwick et al.

(10) Patent No.: US 6,824,704 B2
(45) Date of Patent: Nov. 30, 2004

(54) STABLE TOOTH WHITENING GELS CONTAINING HIGH PERCENTAGES OF HYDROGEN PEROXIDE

(75) Inventors: Thomas C. Chadwick, Nipomo, CA (US); Heather L. Hunt, Grover Beach, CA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 10/684,472

(22) Filed: Oct. 15, 2003

(65) Prior Publication Data

US 2004/0079920 A1 Apr. 29, 2004

Related U.S. Application Data

(60) Continuation of application No. 10/386,656, filed on Mar. 13, 2003, now abandoned, which is a division of application No. 09/428,910, filed on Oct. 28, 1999, now Pat. No. 6,555,020.
(60) Provisional application No. 60/106,076, filed on Oct. 29, 1998.

(51) Int. Cl.$^7$ .................. C09K 15/00; C09K 15/01; C09K 15/055; A61K 7/20; A61K 33/40
(52) U.S. Cl. .................. 252/186.26; 252/186.26; 252/186.29; 124/53; 124/613; 124/616; 433/215; 433/216
(58) Field of Search .................. 252/186.26, 186.28, 252/186.29; 424/53, 613, 616; 433/215, 216

(56) References Cited

U.S. PATENT DOCUMENTS

| | | | |
|---|---|---|---|
| 4,226,851 A | 10/1980 | Sompayrac | 424/53 |
| 4,812,173 A | 3/1989 | Tsao et al. | 134/27 |
| 5,084,268 A | 1/1992 | Thaler | 424/53 |
| 5,098,303 A | 3/1992 | Fischer | 433/215 |
| 5,165,424 A | 11/1992 | Silverman | 128/861 |
| 5,248,389 A | 9/1993 | Heimburger et al. | 162/76 |
| 5,290,566 A | 3/1994 | Schow et al. | 424/488 |
| 5,326,685 A | 7/1994 | Gaglio et al. | 433/215 |
| 5,376,006 A | 12/1994 | Fischer | 433/215 |
| 5,422,073 A | 6/1995 | Mowrey-McKee et al. | 422/28 |
| 5,500,186 A | 3/1996 | Mowrey-McKee et al. | 422/28 |
| 5,593,637 A | 1/1997 | Mowrey-McKee et al. | 422/28 |
| 5,631,000 A | 5/1997 | Pellico et al. | 424/53 |
| 5,641,386 A | 6/1997 | Boelema et al. | 162/76 |
| 5,718,886 A | 2/1998 | Pellico | 424/53 |
| 5,725,843 A | 3/1998 | Fischer | 424/49 |
| 5,756,045 A | 5/1998 | Mowrey-McKee et al. | 422/28 |
| 5,759,440 A | 6/1998 | Van Hemelrijk | 252/186.29 |
| 5,785,527 A | 7/1998 | Jensen et al. | 433/215 |
| 5,851,512 A | 12/1998 | Fischer | 424/49 |
| 5,858,332 A | 1/1999 | Jensen et al. | 424/53 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,922,307 A | 7/1999 | Montgomery | 424/53 |
| 5,985,249 A | 11/1999 | Fischer | 424/49 |
| 5,989,569 A | 11/1999 | Dirksing et al. | 424/401 |
| 6,458,340 B1 | 10/2002 | Ibsen et al. | 424/53 |

Primary Examiner—Joseph D. Anthony
(74) Attorney, Agent, or Firm—Fish & Richardson P.C.

(57) ABSTRACT

An aqueous gel useful for bleaching teeth comprising: (i) water; (ii) polyacrylic acid thickening agent; (iii) hydrogen peroxide bleaching agent; and (iv) aminocarboxylic acid/salt stabilizing agent. Preferably the polyacrylic acid is an easy to disperse carbomer and the gels contain high concentrations (20 to 40% by weight) of hydrogen peroxide. The gels exhibit room temperature stability, both with respect to gel stability and hydrogen peroxide decomposition, sufficient to eliminate the need for constant refrigeration. A method for using the gels to bleach teeth is also disclosed.

3 Claims, No Drawings

STABLE TOOTH WHITENING GELS CONTAINING HIGH PERCENTAGES OF HYDROGEN PEROXIDE

RELATED APPLICATIONS

This application is a continuation of and claims priority to U.S. patent application Ser. No. 10/386,656 filed Mar. 13, 2003, which is a divisional of and claims priority to U.S. patent application Ser. No. 09/428,910 filed Oct. 28, 1999, now U.S. Pat. No. 6,555,020, which claims priority to U.S. Provisional Application Ser. No. 60/106,076 filed Oct. 29, 1998.

TECHNICAL FIELD

This invention pertains to bleaching gels for use in bleaching teeth. More specifically this invention relates to the production of stable aqueous bleaching gels that contain a very high percentage of hydrogen peroxide and methods for their use in bleaching teeth.

BACKGROUND ART

A gel is a colloid produced by combining a dispersed phase with a continuous phase (i.e. a dispersion medium or matrix) to produce a viscous, jelly-like, semisolid material. In the dental industry, gels are utilized as vehicles for applying a variety of dentifrices, bleaching aids, and fluoride compounds to teeth. A "dental bleaching gel" is a gel that carries a bleaching agent that can be safely applied to teeth.

Hydrogen peroxide has become the bleaching agent of choice for use in dental bleaching gels. Hydrogen peroxide is a powerful oxidizer which serves to bleach the colored materials in the teeth, thereby, producing a whiter appearance.

Unfortunately, at room temperature, hydrogen peroxide will attack the gelling agents used to make the dental bleaching gels. As a result of this attack, the gelling agents break down over time. Eventually, the gelling agents break down to such a degree that the gel's viscosity becomes too low to be suitable.

Viscosity is very important to the effectiveness of dental bleaching gels. If the viscosity is too low, the gel will flow uncontrollably from the dispensing tube and become difficult to manipulate for the purposes of varying or equalizing the bleaching treatment applied to the teeth. More importantly, if the viscosity is too low, the gel is more likely to flow away from the teeth, resulting in a reduced residence time. Residence time is the time the dental bleaching gel actually contacts the tooth enamel. The effectiveness of a dental bleaching gel is directly proportional to its residence time.

In addition, hydrogen peroxide tends to decompose at room temperature. The rate of this decomposition is dependent upon many factors. The presence of various metallic impurities, such as iron, manganese, copper and chromium, catalyze the decomposition. Furthermore, the stability of hydrogen peroxide decreases with increasing alkalinity and temperature. Because the whitening ability of a dental bleaching gel depends on the hydrogen peroxide concentration, premature decomposition diminishes the ability of the gel to whiten.

To combat these problems, dental bleaching gels containing high concentrations of hydrogen peroxide are generally refrigerated until immediately prior to use. Refrigeration slows down the hydrogen peroxide attack on the gelling agent and also slows down hydrogen peroxide decomposition. However, refrigeration is both expensive and inconvenient.

Various stabilizing agents have been investigated in an attempt to develop hydrogen peroxide containing dental bleaching gels that are stable at room temperature. Unfortunately, to date, these stabilizing agents have either proven ineffective.

The instant invention solves these stability problems by providing, for the first time, an effective bleaching gel that is stable at room temperature and that contains a large concentration of hydrogen peroxide. There appears to be very little prior art that is relevant to this invention. The most relevant prior art known to the inventors includes the following:

U.S. Pat. Nos. 5,422,073, 5,500,186, 5,593,637 and 5,756,045 teach a method for disinfecting a contact lens which includes contacting the lens with an isotonic aqueous solution comprising 0.6 to 2 weight percent tromethamine. Other aspects include adding to the solution a chelating agent (preferably disodium EDTA) and/or additional microbicide. The microbicide may be a very low concentration of hydrogen peroxide, e.g., 50 to 200 ppm. The disodium EDTA is not used as a stabilizer for the hydrogen peroxide.

U.S. Pat. No. 5,759,440 teaches an aqueous solution (as opposed to a gel) of hydrogen peroxide stabilized by incorporation of a composition containing a mixture of an alkali metal pyrophosphate or alkaline earth metal pyrophosphate with a stabilizer belonging to the category of aminopolycarboxylic acids. The solution finds application for bleaching textiles and paper pulps.

U.S. Pat. No. 5,641,386 teaches a process for the bleaching of pulp comprising the step of bleaching the pulp with hydrogen peroxide and an effective amount of at least one biodegradable 1-amino-alkane-1,1-diphosphate chelating agent to enhance the bleaching of the pulp.

U.S. Pat. No. 4,812,173 teaches stabilized hydrogen peroxide disinfecting solutions containing diphosphoric acids (such as hydroxyethylidene diphosphoric acid), and glycerin.

U.S. Pat. No. 5,248,389 teaches a process for peroxygen bleaching of high yield pulp in which sodium carbonate replaces sodium hydroxide and sodium silicate.

U.S. Pat. Nos. 5,098,303, 5,376,006 and 5,725,843 teach high viscosity sustained release dental compositions, such as tooth bleaching or fluoride compositions, for treating tooth surfaces. The sustained release dental compositions include a high carboxypolymethylene concentration (typically greater than 3.5%) which results in very high viscosity. The bleaching gels can contain from about 3 to about 20% carbamide peroxide, preferably about 4% to about 15% carbamide peroxide. Alternatively, the bleaching gels can contain hydrogen peroxide in a preferred range of from about 2% to about 10%.

U.S. Pat. No. 4,226,851 teaches a stable dental hygiene composition comprising a mixture of hydrogen peroxide and zinc chloride. The mixture is stabilized by the addition of water soluble vitamin E.

Ultradent, produced by Ultradent Products of South Jordan, Utah, offers a 35% hydrogen peroxide bleaching gel product called Opalescence Xtra. The package contains a prominent warning which states "REFRIGERATION REQUIRED!" Similar warnings appear in two places on the package insert. Opalescence Xtra is a gel that is red in color due to the presence of β-carotene. Opalescence Xtra turns into a colorless, runny liquid in less than two weeks when stored at room temperature.

None of the aforementioned references describes the stabilization of gels with respect to both gel stability and hydrogen peroxide stability.

SUMMARY OF THE INVENTION

This invention is directed to aqueous gels useful for bleaching teeth comprising: (i) water; (ii) polyacrylic acid thickening agent; (iii) at least one bleaching agent selected from the group consisting of hydrogen peroxide and compounds that release hydrogen peroxide in water; and (iv) aminocarboxylic acid/salt stabilizing agent. Preferably the gel also comprises (v) a neutralizing agent that serves to neutralize the polyacrylic acid. Ideally, these gels are fast acting bleaching gels that contain 20 to 50% by weight bleaching agent.

The combination of polyacrylic acid thickener and the aminocarboxylic acid/salt stabilizer provides a gel that can be loaded with hydrogen peroxide and remain sufficiently stable to provide a suitable gel (from a viscosity standpoint) after 4 to 12 weeks storage at room temperature. In addition, the gels exhibit little hydrogen peroxide decomposition.

These gels may be applied by a method comprising the following steps: (a) protecting the soft tissue surrounding the teeth with a covering; (b) applying the aforementioned aqueous gel to the teeth; and (c) removing the gel. Preferably, prior to removal, the gel is treated with a laser or heat lamp to accelerate bleaching.

DISCLOSURE OF THE INVENTION

As stated, the instant invention is directed to aqueous gels that contain hydrogen peroxide and that are stable at room temperature for up to twelve weeks. These gels comprise: (i) water; (ii) thickening agent; (iii) bleaching agent; (iv) stabilizing agent; and, optionally, (v) neutralizing agent.

Water is the principle component of the aqueous gels. Preferably, water is present in an amount over 50% by weight. More preferably, water makes up the remainder of the gel after removal of the thickening agent, bleaching agent, stabilizing agent and neutralizing agent.

The thickening agent (a.k.a. gelling agent) is present in an amount ranging from 0.25% to 3% by weight of the aqueous gel. The thickening agent is a "polyacrylic acid" which means that it is selected from acrylic acid homopolymers and copolymers comprising 90% or more, by weight, polymerized acrylic acid units. The preferred acrylic acid monomer used to make these thickeners is the actual compound "acrylic acid." However, other acrylic acids can also be employed, e.g. methacrylic acid and $C_{1-4}$ alkyl substituted acrylic acid. Other comonomers that may be present in the polymer chain include 10% by weight or less long chain alkyl esters of acrylic acid.

Suitable thickeners include the crosslinked polyacrylic resins sold by B.F. Goodrich under the tradename Carbopol®. The USP-NF, British Pharmacopoeia, United States Adopted Names Council (USAN), and Cosmetic, Toiletries and Fragrance Association (CTFA) have adopted the generic (i.e. non-proprietary) name "carbomer" for the Carbopol® homopolymers. The Japanese Pharmaceutical Exipients list Carbopol® homopolymers as "carboxyvinyl polymer" and "carboxy polymethylene." All of these polymers have the same acrylic acid backbone. The main differences are related to the presence of comonomer and crosslink density. These polymers are either homopolymers of acrylic acid crosslinked with allyl sucrose, polyalkyl ethers of divinyl glycol, or allyl pentaerythritol or similarly crosslinked copolymers of acrylic acid with minor levels of long chain alkyl acrylate comonomers. These polymers swell in water up to 1000 times their original volume (and ten times their original diameter) to form a gel when exposed to a pH environment above 4.0–6.0. Carbopol® thickeners are highly resistant to hydrolysis and oxidation under normal conditions.

Preferred thickeners include Carbopol® ETD™ 2001, Carbopol®ETD™2020, and Carbopol® ETD™ 2050. These "easy-to-disperse (ETD™)" thickeners are homopolymers or copolymers of acrylic acid, produced using a polymerization aid, and crosslinked with a polyalkenyl polyether. Carbopol® ETD™ 2001, Carbopol® ETD™ 2020, and Carbopol® ETD™ 2050 are easier to disperse and mix than other Carbopol® products. The thickeners wet quickly and thereby minimize lumping. By "wet" it is meant that the white particles of polymer fully disappear (disperse) into the mixture. The thickeners also hydrate slowly and have a lower viscosity prior to neutralization than other Carbopol® products. Because of the fast wetting nature and low viscosity of the thickeners, vigorous agitation is not necessary to disperse them. This is important to the instant invention since vigorous agitation is undesirable because it induces hydrogen peroxide decomposition. The fast wetting nature of the thickeners also aids handling. Once the ETD™ resins are neutralized, they provide the type of highly efficient thickening for which Carbopol resins are known.

The most preferred thickener is Carbopol® Ultrez™ 10. This thickener is an exceptionally easy-to-disperse polymer that wets even more quickly than the Carbopol ETD™ resins. In fact, Carbopol® Ultrez™ 10 wets without any stirring. For example, a 500 gram dispersion at 0.5% resin (2.5 grams) will take only about 5 minutes to completely wet without mixing. This decreases the time and effort necessary to achieve a lump-free dispersion.

The bleaching agent utilized in the aqueous gel is present in an amount ranging from 3 to 50%, preferably 20 to 50%, more preferably 30–40%, and most preferably 35% by weight of the aqueous gel. Higher amounts of bleaching agent are preferred so that the gel may serve as a "fast acting bleaching gel" capable of bleaching teeth with only one or two applications.

The bleaching agent may be selected from hydrogen peroxide ($H_2O_2$) or any compound that yields hydrogen peroxide when placed in an aqueous medium. In example, carbamide peroxide ($CO(NH_2)_2H_2O_2$) generates hydrogen peroxide when placed in water. Other names for carbamide peroxide include urea peroxide, urea hydrogen peroxide, hydrogen peroxide carbamide, and perhydrol urea.

The stabilizing agent utilized in the aqueous gel is present in an amount ranging from 0.05 to 0.5% by weight of the aqueous gel. An amount of approximately 0.15% stabilizer is preferred. The stabilizing agent is selected from aminocarboxylic acids and salts thereof. Preferred stabilizers are selected from aminocarboxylic acids and alkali and/or alkali earth metal salts thereof. Suitable aminocarboxylic acids include trans-1,2-cyclohexylene dinitrilotetraacetic acid (CDTA), ethylenediamine tetraacetic acid (EDTA), N-(2-hydroxyethyl) ethylenediamine triacetic acid (HEDTA), Nitrilotriacetic acid (NTA), diethylene triamine pentaacetic acid (DTPA), triethylene tetraamine hexaacetic acid (TTHA), and ethyleneglycol bis (2-aminoethylether) tetraacetic acid (GEDTA). The most preferred stabilizers include CDTA, $CaNa_2EDTA$, $Na_2EDTA$, $Na_4EDTA$, HEDTA, and $Na_3HEDTA$.

The combination of polyacrylic acid thickener and aminocarboxylic acid/salt stabilizer provides a gel that can be loaded with hydrogen peroxide and that is stable in the sense that it maintains a suitable gel for 4 to 12 weeks at room temperature. For example, a 3.4/1 ratio of polyacrylic acid/

CaNa$_2$EDTA yields an aqueous gel that is stable for 12 weeks, a 3.5/1 ratio of polyacrylic acid/CDTA yields an aqueous gel that is stable for 7 weeks, and a 0.3/1 ratio of polyacrylic acid/Na$_2$EDTA yields a gel that is stable for 4 1/2 weeks. By "suitable gel" it is meant that when a drop of the gel is placed on the surface of a flat glass plate and the surface is turned vertically, the gel droplet remains in place on the plate surface. It is not certain why the results obtained using different aminocarboxylic acid/salt stabilizers vary. What is certain is that the polyacrylic acid thickener is more resistant to attack than many other thickeners and that the presence of an aminocarboxylic acid/salt stabilizer can enhance this stability many fold.

In addition, the stabilizer prevents substantial hydrogen peroxide decomposition at room temperature. Hydrogen peroxide loss in gels utilizing polyacrylic acid thickeners and aminocarboxylic acid/salt stabilizers is less than 0.05% by weight per day.

The end result is that the aqueous gels can now be produced that have commercially viable shelf-lives at room temperature. Thus, constant refrigeration, which is both expensive and inconvenient, is no longer necessary.

In addition to the aforementioned components, a neutralizing agent may be added to the aqueous gel. The presence of a neutralizing agent is preferred since it serves to further thicken the system. The neutralization agent ionizes the polyacrylic acid and generates negative charges along the backbone of the polymer. Repulsions of like charges then cause uncoiling of the polymer into an extended structure. This reaction is rapid and gives instantaneous thickening.

The inorganic and organic neutralizing agents which may be employed are bases. Suitable bases include alkali metal hydroxides and ammonium hydroxide, carbonates, alkoxides, oxides, peroxides, superoxides, and water soluble organic amines. Amino acids such as β-alanine and lysine can also be used for neutralization and viscosity modification. Preferred bases include sodium hydroxide, potassium hydroxide, ammonium hydroxide, triethanolamine (TEA), aminomethyl propanol (AMP), 2-amino-2-hydroxymethyl-1,3-propanediol (Tromethamine), tetrahydroxypropyl ethylenediamine, and tris(hydroxymethyl)aminomethane (TRIS). The amount of base utilized is the amount of base necessary to fully neutralize the polyacrylic acid thickener in the aqueous gel. This amount will vary considerably depending on the nature of the base and the amount of polyacrylic acid. In example, the following Table 1 sets forth the amount of different bases required to neutralize polyacrylic acid to an appropriate pH of 6.0–7.0:

TABLE 1

| Base | Relative ratio of base to one part polyacrylic acid by weight |
| --- | --- |
| Sodium hydroxide (18% solution) | 0.5 |
| Potassium hydroxide (18% solution) | 0.5 |
| Ammonium hydroxide (28% solution) | 0.3 |
| Triethanolamine (TEA) | 2.0 |
| Tromethamine (2-Amino-2-Hydroxymethyl-1,3-propandiol) | 2.0 |
| Aminomethyl propanol (AMP) | 1.5 |
| Tetrahydroxypropyl ethylene diamine | 2.0 |

The dental bleaching gel of the instant invention can be applied to the teeth in a number of ways. In example, the gel can be applied to the teeth using a brush, syringe, tray, or any other application means.

In a typical treatment process, the soft tissues surrounding the teeth are first covered with a protecting device, e.g. a ligated rubber dam. This is important because the more hydrogen peroxide a dental bleaching gel contains, the more likely it is to burn the soft tissue upon contact. Dental bleaching gels containing at least 30% by weight hydrogen peroxide will immediately burn any soft tissue they contact, quickly turning the tissue white.

Next a brush, needle, or some other delivery system is utilized to place the dental bleaching gel described above in contact with the teeth one wishes to bleach. Most patients only request treatment on the labial surfaces of the 6 to 8 front teeth which show most prominently when one smiles.

The dental bleaching gel is then allowed to remain in contact with the teeth for a period of time ranging anywhere from 5 minutes to one hour. Preferably, however, this contact period ranges from 20 to 30 minutes. As stated earlier, the bleaching effect of any dental bleaching gel is directly proportional to this residence time.

The bleaching effect of the hydrogen peroxide in a given period of time can be amplified by applying a heat lamp or laser light to the dental bleaching gel once it is in place on the teeth. The heat and light serve to increase the rate of bleaching of the hydrogen peroxide, providing a shorter period of time for whitening the teeth.

Once the treatment is done, the gel is removed with a gauze or some other means. The patient's mouth is then thoroughly cleaned with water and suction. When the dental bleaching gel comprises at least 20% by weight hydrogen peroxide, only one or two such treatments are necessary.

The following examples are illustrative of the invention:

EXAMPLES 1–19

Various blends of powdered stabilizer (or aqueous solution in the case of Versenol 120) and powdered thickening agent were weighed in a plastic or glass beaker. Aqueous hydrogen peroxide was then added to the blends in the amount of 35% (w/w). The mixtures were gently stirred until the powdered ingredients fully dissolved. This completed the procedure in the blends wherein carboxymethylcellulose, xanthan gum, and carrageenan were used as the thickeners. In the blends containing polyacrylic acid as the thickener, triethanolamine was also added. All of the gels were then packaged in 10 mL polyethylene syringes. The composition of each blend formulation is set forth in the following Table 2:

TABLE 2

| Example | Gelling agent (grams) | Stabilizer (grams) | 35% H$_2$O$_2$ (grams) | Triethanolamine (grams) |
| --- | --- | --- | --- | --- |
| 1 | 0.102 Polyacrylic acid[1] | — | 20.00 | 0.050 |
| 2 | 0.102 Polyacrylic acid | 0.030 CaNa$_2$EDTA[5] | 20.00 | 0.050 |
| 3 | 0.412 Xanthum Gum[2] | 0.030 CaNa$_2$EDTA | 20.00 | — |
| 4 | 0.514 Xanthum Gum | 0.031 CaNa$_2$EDTA | 20.00 | — |
| 5 | 0.612 Carboxymethyl cellulose[3] | 0.030 CaNa$_2$EDTA | 20.00 | — |
| 6 | 1.262 Sodium carrageenan[4] | 0.030 CaNa$_2$EDTA | 20.00 | — |
| 7 | 0.102 Polyacrylic acid | 0.0294 CDTA[6] | 20.00 | 0.150 |

TABLE 2-continued

| Example | Gelling agent (grams) | Stabilizer (grams) | 35% $H_2O_2$ (grams) | Tri-ethanol-amine (grams) |
|---|---|---|---|---|
| 8 | 0.102 Polyacrylic acid | 0.0310 $Na_2$EDTA | 20.00 | 0.100 |
| 9 | 0.102 Polyacrylic acid | .0309 $Na_4$EDTA | 20.00 | 0.100 |
| 10 | 0.102 Polyacrylic acid | 0.0972 $Na_3$HEDTA*[7] | 20.00 | 0.100 |
| 11 | 0.102 Polyacrylic acid | 0.10 Vitamin E*[8] and 0.030 $CaNa_2$EDTA | 20.00 | 0.100 |
| 12 | 0.1025 Polyacrylic acid | 0.0312 $Na_3$NTA*[9] | 20.0189 | 0.250 |
| 13 | 0.1021 Polyacrylic acid | 0.0318 $Na_2$NTA | 20.0366 | 0.200 |
| 14 | 0.1032 Polyacrylic acid | 0.0309 NaCaHEDTA | 20.0029 | 0.050 |
| 15 | 0.1022 Polyacrylic acid | 0.0370 $NaCa_2$DTPA*[10] | 20.0305 | 0.200 |
| 16 | 0.1020 Polyacrylic acid | 0.0300 NaCaNTA | 20.0000 | 0.300 |
| 17 | 0.1026 Polyacrylic acid | 0.0311 $Ca_3$TTHA*[11] | 20.0126 | 0.200 |
| 18 | 0.1019 Polyacrylic acid | 0.0311 $Na_2Ca_2$TTHA | 20.0339 | 0.100 |
| 19 | 0.1024 Polyacrylic acid | 0.0313 $Na_2$CaGEDTA*[12] | 20.0032 | 0.100 |

*[1]Available from B.F. Goodrich and called Ultrez 10
*[2]Available from Aldrich
*[3]Available from Van Waters & Rogers, Inc.
*[4]Available from FMC Corporation
*[5]EDTA = Ethylenediamine tetraacetic acid
*[6]CDTA = trans-1,2-cyclohexylene dinitrilo tetraacetic acid
*[7]HEDTA = N-(2-hydroxyethyl)ethylenediamine triacetic acid which is available as Versenol 120 from Dow Chemical Corp.
*[8]Vitamin E = (DL-α-Tocopherol) and is available from Fluka Chemie
*[9]Nitrilotriacetic acid
*[10]DTPA = Diethylene triamine pentaacetic acid
*[11]TTHA = Triethylene tetramine hexaacetic acid
*[12]GEDTA = Ethyleneglycol bis (2-aminoethylether) tetraacetic acid Gel stability was evaluated by placing a drop of each gel onto the surface of a flat glass plate. The plate was then tilted so that the flat surface was vertical. Gels were considered unsatisfactory when the gel droplet would not remain in place on the plate surface.

Hydrogen peroxide stability was evaluated by iodometric titration. For more information concerning this test see page 854 of "Quantitative Chemical Analysis," 4th edition, 1969, written by I. M. Kolthoff, E. B. Sandell, E. J. Meehan and Stanley Bruckstein, and published by The Macmillan Company/Collier-Macmillan Limited in London, which is herein incorporated by reference. Peroxide concentrations as a function of time were fitted to a zero order kinetic model, and the zero order rate constant (% peroxide loss per day) was used to measure peroxide stability. The tendency of the gels to produce oxygen during storage was also observed. This was done in two ways. First, any displacement of the syringe plunger was noted during each sampling interval. Second, any gel that expelled from the syringe tip was also noted.

The results of these stability studies are set forth in the following Table 3, wherein each example corresponds to a like numbered example in Table 2:

TABLE 3

| Example | Days as a satisfactory gel | k (% $H_2O_2$ per day) | Self-expelling |
|---|---|---|---|
| 1 | 7 | 0.04 | Yes |
| 2 | 84 | −0.004 | No |
| 3 | 28 | 0.0002 | No |
| 4 | 28 | −0.01 | No |
| 5 | 7 | −0.01 | Yes |
| 6 | 7 | −0.05 | No |
| 7 | 48 | −0.004 | No |
| 8 | 33 | −0.05 | Yes |
| 9 | 57 | −0.01 | No |
| 10 | 44 | 0.01 | Yes |
| 11 | 18 | 0.01 | No |
| 12 | 8 | −0.001 | ? |
| 13 | 8 | −0.01 | ? |
| 14 | <5 | −0.03 | No |
| 15 | 3 | — | No |
| 16 | <3 | — | Yes |
| 17 | <7 | −0.01 | No |
| 18 | <7 | −0.02 | No |
| 19 | <3 | — | No |

Examples 2–6 demonstrate the variations in stability that result from using different gelling agents with identical amounts of stabilizer ($CaNa_2$EDTA) and identical amounts of hydrogen peroxide. As can be seen, the polyacrylic acid thickening agent Ultrez 10 is by far the best gelling agent from the standpoint of gel stability, although xanthan gum provides a gel with reasonably good stability. Carboxymethylcellulose and carageenan were not satisfactory. A comparison of Examples 1 and 2 demonstrates that the presence of the $CaNa_2$EDTA stabilizer greatly enhances the gel stability provided by polyacrylic acid thickening agents.

Examples 7–19 demonstrate how the stability of gels utilizing polyacrylic acid gelling agents varies depending on the quantity and type of aminocarboxylic acid stabilizer employed. As can be seen, the best stabilizers are ETDA and its salts, CDTA, and HEDTA. These stabilizers form gels which have good gel stability, good hydrogen peroxide stability and a low tendency to produce oxygen gas. Note that some of the gels have positive zero order constants for hydrogen peroxide decomposition. This is thought to be due to a very low rate of hydrogen peroxide decomposition in combination with a much higher rate of water evaporation.

While the invention has been described in conjunction with the specific embodiments outlined above, it is evident that many alternatives, modifications, and variations will be apparent to those skilled in the art. Accordingly, the preferred embodiments of the invention are intended to be illustrative and not limiting. Various changes may be made without departing from the spirit and scope of the invention as defined in the claims.

What is claimed is:

1. A method for bleaching teeth comprising the following steps:
    (a) protecting the soft tissue surrounding the teeth with a covering;
    (b) applying an aqueous dental bleaching gel to the teeth that comprises:
        (i) water;
        (ii) a polyacrylic acid thickening agent;
        (iii) at least one bleaching agent selected from the group consisting of hydrogen peroxide and compounds that release hydrogen peroxide in water; and
        (iv) a stabilizing agent selected from the group consisting of EDTA, CDTA, and a salt thereof,
    wherein said bleaching agent is present in an amount ranging from about 20% to about 50% by weight, and wherein said polyacrylic acid thickening agent and said stabilizing agent are added in a weight ratio within the range of about 3.3:1 to about 3.5:1 that maintains said aqueous gel in a suitable gel form for 4 to 12 weeks at room temperature in a syringe plunger without self-expelling; and (c) removing the dental bleaching gel.

2. The method of claim 1 wherein the dental bleaching gel remains in contact with the teeth for a period of 5 to 60 minutes.

3. The method of claim 2 wherein the dental bleaching gel is applied to the teeth and then treated with a laser light or heat lamp prior to removal.

* * * * *